(12) United States Patent
Holland et al.

(10) Patent No.: US 8,870,952 B2
(45) Date of Patent: Oct. 28, 2014

(54) VALVE ASSEMBLIES FOR IMPLANTABLE PROSTHESES AND TISSUE EXPANDERS

(71) Applicants: Petra Gerarda Holland, Rotterdam (NL); Petra C M van Schie, Bergschenhoek (NL)

(72) Inventors: Petra Gerarda Holland, Rotterdam (NL); Petra C M van Schie, Bergschenhoek (NL)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/706,496

(22) Filed: Dec. 6, 2012

(65) Prior Publication Data

US 2014/0163677 A1    Jun. 12, 2014

(51) Int. Cl.
*A61F 2/12* (2006.01)
*F16K 15/20* (2006.01)

(52) U.S. Cl.
CPC ........... *A61F 2/12* (2013.01); *A61F 2250/0003* (2013.01); *F16K 15/202* (2013.01)
USPC .......................................................... 623/8

(58) Field of Classification Search
CPC .................................. A61F 2/12; A61B 19/00
USPC .............................................. 623/8; 137/844
See application file for complete search history.

(56) References Cited

U.S. PATENT DOCUMENTS

| | | | |
|---|---|---|---|
| 2,568,976 A | 9/1951 | Andrews |
| 4,263,682 A | 4/1981 | Bejarano |
| 4,662,883 A | 5/1987 | Bell et al. |
| 4,775,379 A | 10/1988 | Fogarty et al. |
| 4,930,535 A | 6/1990 | Rinehold |
| 4,944,749 A | 7/1990 | Becker |
| 5,019,101 A | 5/1991 | Purkait et al. |
| 5,456,716 A | 10/1995 | Iversen et al. |
| 5,507,808 A | 4/1996 | Becker |
| 2011/0160854 A1 | 6/2011 | Berg et al. |

FOREIGN PATENT DOCUMENTS

EP    0400628 A1    12/1990

*Primary Examiner* — Bruce E Snow
*Assistant Examiner* — Brian Dukert

(57) ABSTRACT

An expandable implant includes an implant shell having an opening and a valve assembly closing the opening. The valve assembly has a first elastic patch, and a second elastic patch juxtaposed with the first elastic patch. A major face of the first elastic patch opposes a major face of the second elastic patch, and the opposing major faces have a bonded area in which the opposing faces are joined together and an unbonded area in which the opposing faces are not joined together and are free to move away from one another. A plug is disposed between the opposing major faces. A first opening extends through the first elastic patch and a second opening extends through the second elastic patch. The first and second openings are offset from one another and the unbonded area defines an elongated channel extending between the first and second openings.

21 Claims, 10 Drawing Sheets

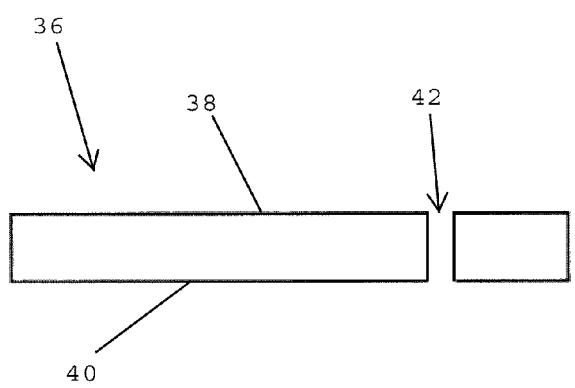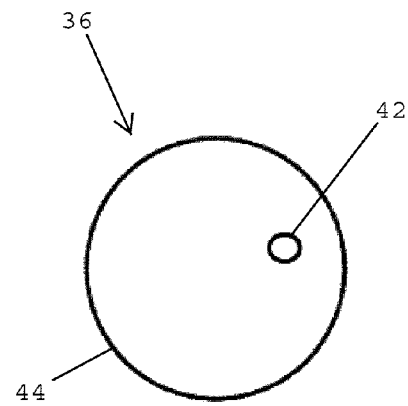
FIG. 2A　　　　　　　　　　FIG. 2B
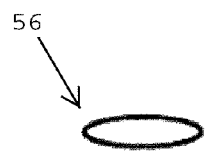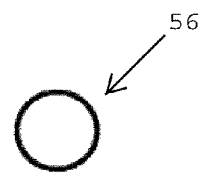
FIG. 4A　　　　　　　　　　FIG. 4B
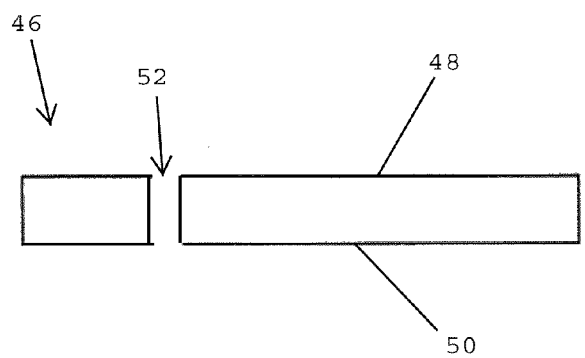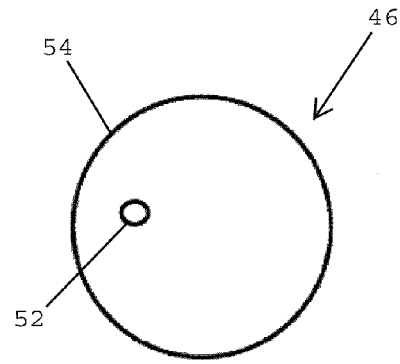
FIG. 3A　　　　　　　　　　FIG. 3B

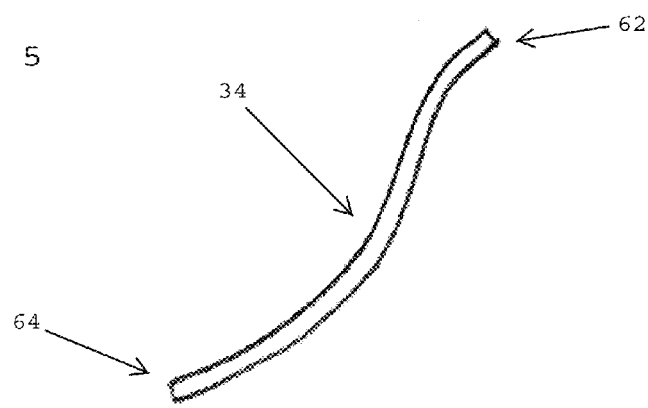
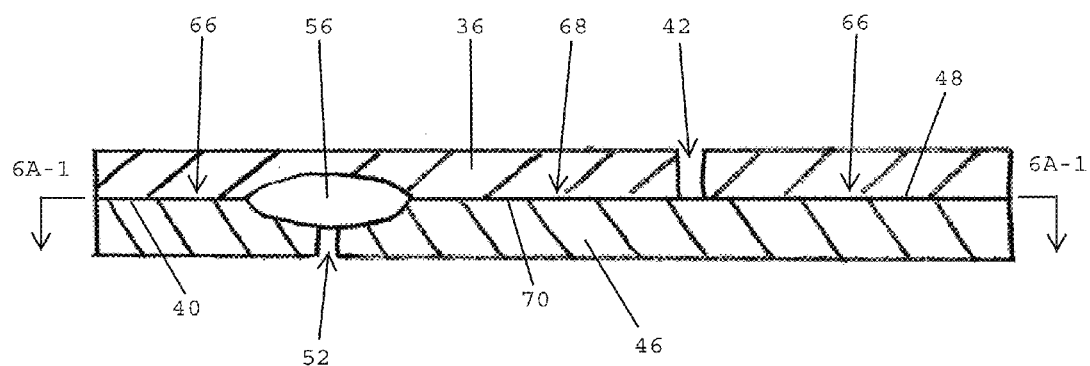

VALVE ASSEMBLIES FOR IMPLANTABLE PROSTHESES AND TISSUE EXPANDERS

BACKGROUND OF THE INVENTION

1. Field of the Invention

The present invention generally relates to medical devices, and more specifically relates to implantable prostheses and tissue expanders.

2. Description of the Related Art

Implantable prostheses are commonly used to replace or augment body tissue. In the case of the female breast, it may become necessary to remove some or all of the mammary gland and surrounding tissue in order to treat breast cancer. This surgery leaves a void that can be filled with an implantable prosthesis that supports surrounding tissue and provides a normal body appearance, eliminating much of the shock and depression that often follows breast cancer surgeries. Implantable prostheses are also used for breast augmentation procedures.

Tissue expanders are implantable devices that are placed beneath the skin and then gradually inflated to stretch the overlying tissue. Tissue expanders are commonly used to either create a pocket for receiving a permanent prosthesis or to generate an increased skin surface area in anticipation of the new skin being utilized for grafting or reconstruction. After implantation, a solution, such as saline, is periodically injected into the tissue expander to increase the volume of the expander. Between injections, the surrounding skin is permitted to stretch and grow to create the increased skin surface. The solution may also be withdrawn from the tissue expander to reduce its volume.

Implantable prostheses and tissue expanders are usually formed of a silicone shell. Such devices are typically manufactured by dipping an appropriately sized and shaped mandrel into a biocompatible elastomer, such as silicone. Once the shell has been formed, it is removed from the mandrel. The dip-molding process results in the formation of a shell that has a mandrel opening, e.g., a circular hole, in one of its faces. The mandrel opening is subsequently covered with a patch that seals the hole to form a fluid impervious implant shell. The patch may be attached to the implant shell using silicone rubber or other similar biocompatible adhesives. The completed shell can remain unfilled, be pre-filled, or intraoperatively filled through a small fill port or valve with a solution such as saline, gel, foam, or combinations of these materials.

Valve assemblies are often used for post-operative filling and adjustment of implantable prostheses and tissue expanders. The valve assemblies used in these implants tend to be large and palpable. Permanent implants, e.g., breast implants, have filling tubes which may be used to add and withdraw fluid, however, these implants typically do not allow for adjustment after the filling tube is removed. As such, the pathway left after withdrawal of the tube is permanently closed.

There have been many efforts directed to providing valves for implants. U.S. Pat. No. 4,263,682 discloses a self-sealing valve for a fluid fillable implant, such as a mammary prosthesis, having first and second planar members that are bonded together in such a manner that leaves a bonded region and an elongated, unbonded region therebetween. Openings are formed in the planar members of the valve to provide for communication between the unbonded region and the inside and outside of the valve. The openings are offset from one another so that the openings and the unbonded region form a normally open channel through the valve. At least one of the planar members is sufficiently flexible to close the normally open channel is response to fluid pressure from within a fluid filled implant. Unfortunately, in use, it has been observed that the interior fluid pressure is not sufficient to prevent leakage of fluid through the valve.

In spite of the above advances, there remains a need for prosthetic implants and tissue expanders having valves that facilitate adding and removing solution from the implant shell. In addition, there remains a need for implants and tissue expanders having valves with a low profile, that are minimally palpable, and that are highly leak resistant. There also remains a need for prosthetic implants and tissue expanders having valve assemblies that enable solution to be easily added and removed both before and after implantation.

SUMMARY OF THE INVENTION

In one embodiment, an expandable implant preferably includes an implant shell having an outer surface, an inner surface, an opening extending from the outer surface to the inner surface, and a valve assembly that closes the opening in the implant shell. In one embodiment, the valve assembly has a first elastic patch and a second elastic patch juxtaposed with the first elastic patch, whereby a major face of the first elastic patch opposes a major face of the second elastic patch. In one embodiment, the opposing major faces define a bonded area in which the opposing major faces are joined together and an unbonded area in which the opposing major faces are not joined together and are free to move away from one another.

In one embodiment, the valve assembly for the implant has a plug disposed between the opposing major faces of the first and second elastic patches. The plug preferably has less elasticity than the first and second elastic patches. In one embodiment, a first opening extends through the first elastic patch and is in communication with the unbonded area between the opposing major faces, and a second opening extends through the second elastic patch and is also in communication with the unbonded area between the opposing major faces, whereby the second opening is offset from the first opening. In one embodiment, the unbonded area between the opposing major faces of the elastic patches includes a channel extending between the first and second openings of the first and second elastic patches. In one embodiment, the channel extending between the first and second openings is elongated, and the opposing major faces of the elastic patches are free to move away from one another within the elongated channel.

In one embodiment, the implant preferably includes a filling tube extending through the valve assembly from outside the implant shell to inside the implant shell for opening the valve assembly for inflating and deflating the implant. In one embodiment, the filling tube is flexible and made of a biocompatible material. In one embodiment, the filling tube passes through the first opening in the first elastic patch, through the elongated channel between the first and second openings, around a first section of an outer surface of the plug, and through the second opening in the second elastic patch.

In one embodiment, the first section of the outer surface of the plug is unbonded to the second elastic patch so that the section of the second elastic patch that opposes the first section of the plug is free to move away from the plug. In this embodiment, however, a second section of the outer surface of the plug is preferably bonded to another section of the second elastic patch, and a third section of the outer surface of the plug is preferably bonded to the first elastic patch.

In one embodiment, the plug is disposed between the opposing major faces of the first and second elastic patches.

In one embodiment, the plug is aligned with the second opening in the second elastic patch.

In one embodiment, the first and second elastic patches are desirably substantially planar, and the plug may have a circular, ellipsoid, oblate spheroid, square or rectangular shape. In one embodiment, the plug has a thickness that is greater than the thickness of each of the first and second elastic patches. In one embodiment, the plug has a thickness of about 2-5 mm, and each of the elastic patches has a thickness of about 0.25-1.0 mm.

In one embodiment, a valve assembly for an expandable implant, such as a breast implant or a tissue expander, desirably includes a first elastic patch, and a second elastic patch juxtaposed with the first elastic patch, whereby a major face of the first elastic patch opposes a major face of the second elastic patch. In one embodiment, the opposing major faces have a bonded area in which the opposing major faces are joined together and an unbonded area in which the opposing major faces are free to move away from one another. In one embodiment, the unbonded area is surrounded by the bonded area.

In one embodiment, the valve assembly includes a first opening extending through the first elastic patch, which is in communication with the unbonded area, and a second opening extending through the second elastic patch, which is also in communication with the unbonded area. In one embodiment, the second opening is offset from the first opening.

In one embodiment, the unbonded area defines an elongated channel extending between the first and second openings and the opposing major faces of the first and second elastic patches. Within the unbonded area, the opposing major faces aligned with the elongated channel are free to move away from one another.

In one embodiment, the valve assembly includes a plug disposed between the opposing major faces of the first and second elastic patches. The plug may have a circular, spheroid, oblate spheroid, ellipsoid, square or rectangular shape. The plug desirably has less elasticity than the first and second elastic patches. In one embodiment, the relatively less elastic plug causes stress between the first and second elastic patches for closing the first and second openings when the filling tube is removed from the valve assembly.

In one embodiment, a filling tube is passable through the first opening, through the elongated channel, around at least a first section of an outer surface of the plug, and through the second opening.

In one embodiment, the plug has an outer surface including the first section that is in contact with, but unbonded to the second elastic patch, a second section that is bonded to the second elastic patch, and a third section that is bonded to the first elastic patch.

In one embodiment, the plug has a thickness that is greater than the thickness of each of the first and second elastic patches. In one embodiment, the plug has a thickness of about 2-5 mm and a diameter of about 7-12 mm. In one embodiment, each elastic patch has a thickness of about 0.25-1.0 mm and a diameter of about 30-50 mm.

In one embodiment, the plug may be made of a material such as silicone, vulcanized silicone, silicone gel, LSR elastomer, and high-consistency elastomer. In one embodiment, the elastic patches may be made of silicone, LSR elastomer, and high-consistency elastomer.

In one embodiment, a valve assembly for an expandable implant desirably includes a first elastic patch, and a second elastic patch juxtaposed with the first elastic patch, whereby the opposing major faces of the elastic patches have a bonded area in which the opposing major faces are joined together and an unbonded area in which the opposing major faces are free to move away from one another. A plug is disposed between the opposing major faces of the first and second elastic patches, whereby the plug has less elasticity than the first and second elastic patches.

In one embodiment, a first opening extending through the first elastic patch is in communication with the unbonded area, and a second opening extending through the second elastic patch is also in communication with the unbonded area. The first and second openings are offset from one another.

In one embodiment, the unbonded area between the opposing faces defines an elongated channel extending between the first and second openings of the respective first and second elastic patches. A filling tube is passable through the first opening, the elongated channel, around at least a section of the outer surface of the plug, and through the second opening for opening the valve assembly for inflating and deflating an implant shell.

In one embodiment, a plug is inserted between the two elastic patches, which causes stress between the two layers of the patch for closing the elongated channel between the first opening in the first elastic patch and the second opening in the second elastic patch. In one embodiment, the plug is less elastic than the first and second elastic patches. The plug may have a variety of shapes including circular, coin-shaped, oblate spheroid, ellipsoid, square, and rectangular.

In one embodiment, after the parts of the valve are assembled together, the parts are bonded, such as by vulcanization. In one embodiment, during assembly of the valve, a polymer strip (e.g., Teflon, Mylar) is placed in between the two elastic patches to form the elongated channel connecting the first and second openings in the respective patches. In one embodiment, a Teflon ring may be placed in between the two elastic patches to create a pocket for the plug. In one embodiment, the valve components may also be glued together or molded together as one component. The plug may also be inserted after the two elastic patches are assembled together.

In one embodiment, the filling tube may be inserted before the valve assembly is secured to the shell of the implant or tissue expander. Once the valve assembly is prepared, it can be joined to the breast implant shell by means of vulcanization, adhesive or glue.

The plug may be made from vulcanized silicone, silicone gel, LSR elastomer, or a high-consistency elastomer. In one embodiment, the elastic patches are made of silicone, such as a high-consistency elastomer. In one embodiment, the elastic patches may be molded from LSR elastomer.

In one embodiment, the valve has a diameter of about 40 mm, but may have a smaller or larger diameter depending upon the implant device for which it is used. Each of the first and second elastic patches has a thickness of about 0.25-1.00 mm and more preferably about 0.50 mm. Each plug has a thickness of about 2-5 mm and a diameter of about 5-15 mm and more preferably about 10 mm.

In one embodiment, inserting the filling tube into the valve assembly serves to open the valve and allow inflation and deflation of the device. When the filling tube is removed, the thickness of the plug relative to the first and second elastic patches causes stress between the two elastic layers of the valve assembly, which closes the openings. Fluid pressure from inside the implant increases the force at which the plug is pressed against the two elastic layers, thus further increasing the sealing effect.

These and other preferred embodiments of the present invention will be described in more detail below.

BRIEF DESCRIPTION OF THE DRAWING

FIG. 2A shows a cross-sectional view of the first elastic patch shown in FIG. 1, in accordance with one embodiment of the present invention.

FIG. 2B shows a top plan view of the first elastic patch shown in FIG. 2A.

FIG. 3A shows a cross-sectional view of the second elastic patch shown in FIG. 1, in accordance with one embodiment of the present invention.

FIG. 3B shows a top plan view of the second elastic patch shown in FIG. 3A.

FIG. 4A shows a cross-sectional view of the plug shown in FIG. 1, in accordance with one embodiment of the present invention.

FIG. 4B shows a top plan view of the plug shown in FIG. 4A.

FIG. 5 shows a filling tube for an implant, in accordance with one embodiment of the present invention.

FIG. 6A-1 shows a cross-sectional view of the valve assembly of FIG. 6A taken along line 6A-1 thereof.

DETAILED DESCRIPTION

Figure 1:
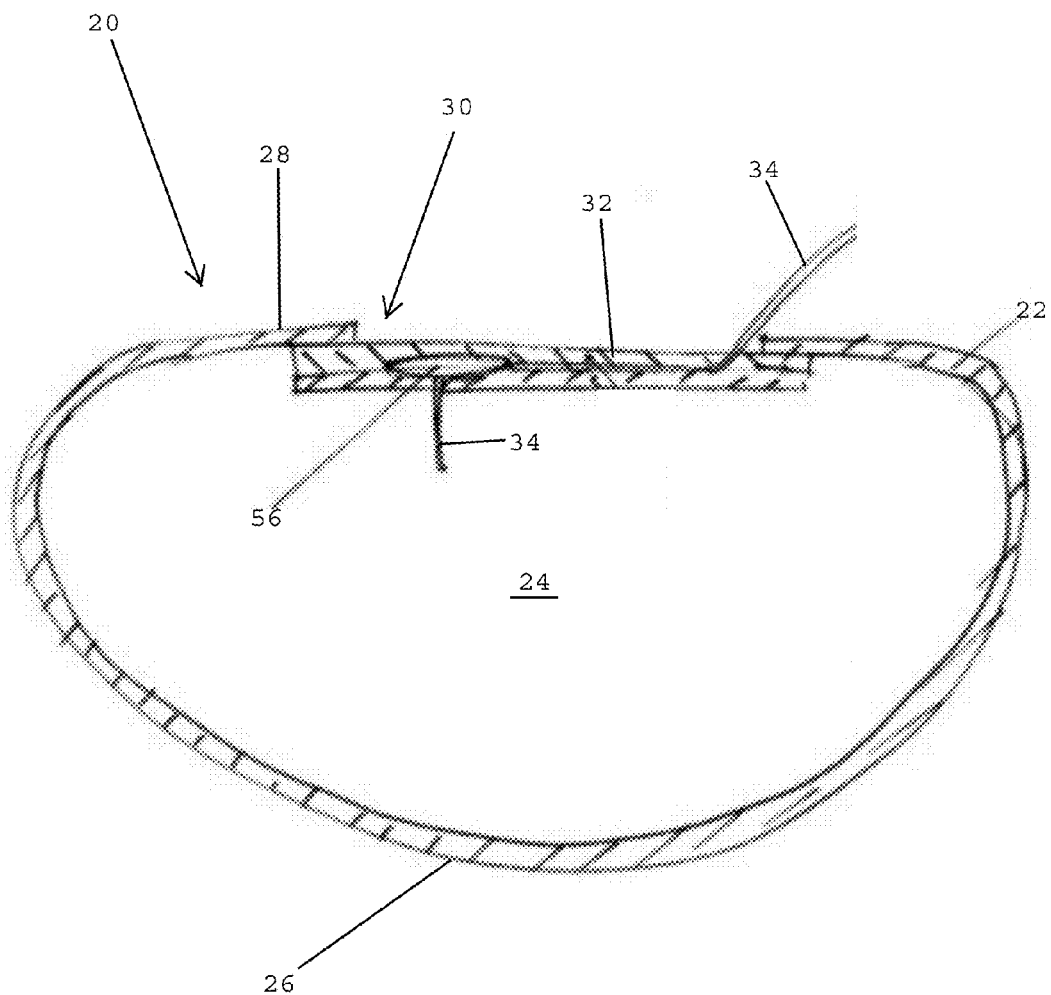
FIG. 1 shows a cross sectional view of an implant having an implant shell and a valve assembly including a first elastic patch, a second elastic patch, a plug disposed between the first and second elastic patches, and a filling tube extending through the valve assembly, in accordance with one embodiment of the present invention.

Referring to FIG. 1, in one embodiment, an implant 20, such as a breast implant or a tissue expander, preferably includes an implant shell 22, such as a silicone shell, that defines an internal chamber 24 adapted to receive a liquid solution, such as saline solution, a gel, or a saline-gel combination. The implant shell 22 preferably has an anterior face 26 and a posterior face 28 with an opening 30 that is closed by a valve assembly 32. A filling tube 34 is passable through the valve assembly. The liquid solution may be added to the implant 20 through the filling tube 34 for expanding the size of the implant, or removed from the implant for reducing the size of the implant.

Referring to FIG. 2A, in one embodiment, the valve assembly includes a first elastic patch 36 having a first planar surface 38, a second planar 40 and a first opening 42 that extends from the first planar surface to the second planar surface. Referring to FIG. 2B, the first elastic patch 36 has an outer edge 44 that has a circular or annular shape. The first elastic patch 36 has the first opening 42 extending through the thickness thereof that is offset from a center of the first elastic patch.

Referring to FIG. 3A, in one embodiment, the valve assembly 32 (FIG. 1) includes a second elastic patch 46 having a top surface 48, a bottom surface 50 and a second opening 52 that extends from the top surface 48 to the bottom surface 50. Referring to FIG. 3B, the second elastic patch 46 has an outer edge 54 that has a circular or annular shape. The second opening 52 that passes through the second elastic patch 46 is offset from a center of the second elastic patch.

Referring to FIGS. 1, 4A, and 4B, in one embodiment, the valve assembly 32 (FIG. 1) includes a plug 56 that is disposed between the first elastic patch 36 and the second elastic patch 46. The plug 56 is preferably less elastic than the first elastic patch 36 and the second elastic patch 46. When viewed from the side (FIG. 4A), the plug 56 has an ellipsoid shape. When viewed from the top (FIG. 4B), the plug 56 has a circular shape. In other embodiments, the plug 56 may have a circular, coin, oblate spheroid, square, or rectangular shape.

Referring to FIG. 5, in one embodiment, a valve assembly for an implant may include an elongated filling tube 34 (FIG. 1) having a first end 62 and a second end 64. The elongated filling tube is flexible and preferably passes through the valve assembly for filling an implant with a solution and/or removing the solution from the implant. After the elongated filling tube 34 has been utilized for expanding or reducing the size of an implant, the elongated filling tube 34 may be removed from the valve assembly for sealing the valve assembly for preventing leakage of solution from the implant.

Figures 1, 6A:
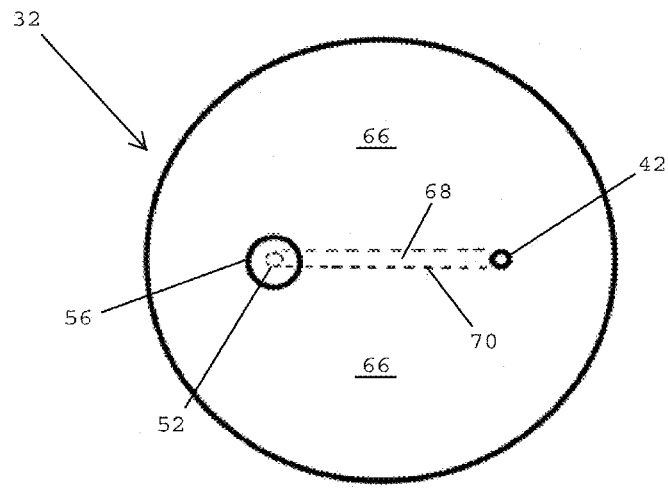
FIG. 6A shows a cross-sectional view of a valve assembly for an implant, in accordance with one embodiment of the present invention.

Referring to FIG. 6A, in one embodiment, the valve assembly is assembled by disposing the plug 56 between the first and second elastic patches 36, 46 and abutting the second surface 40 of the first elastic patch 36 with the first surface 48 of the second elastic patch 46. The first opening 42 through the first elastic patch 36 is offset from the second opening 52 extending through the second elastic patch 46. The plug 56, which is less elastic than the elastic patches 36, 46, is sandwiched between the opposing faces 40, 48 of the respective first and second elastic patches 36, 46.

In one embodiment, the parts of the valve assembly are placed together and secured together by means of vulcanization. In one embodiment, a polymer strip, such as a Mylar or Teflon strip, is placed between the opposing faces 40, 48 of the first and second elastic patches 36, 46 to create an elongated channel extending between the first and second holes 42, 52 of the respective first and second elastic patches 36, 46.

Referring to FIGS. 6A and 6A-1, the opposing contacting surfaces 40, 48 of the respective first and second elastic patches 36, 46 have a major bonded area 66 and a minor unbonded area 68 located inside the major bonded area 66. The minor unbonded area 66 preferably defines an elongated channel 70 that extends between the first opening 42 and the second opening 52. Within the minor unbonded area 68, the opposing major faces 40, 48 of the first and second elastic patches 36, 46 are free to move away from one another in response to stress forces, e.g. when the filling tube 34 (FIG. 1) is advanced from the first opening to the second opening. The opposing surfaces 40, 48 within the major bonded area 66 are bonded and joined together and are not free to move away from one another in response to stress forces.

In one embodiment, the first opening 42 extending through the first elastic patch 36 provides for a fluid path between the outside of the implant and the minor unbonded area 68 of the valve assembly 32. The second opening 52 extending through the second elastic patch 46 provides for communication between the minor unbonded area 68 and the inside of the fluid fillable implant defined by the internal chamber 24 (FIG. 1). The less elastic plug 56 includes a first section 72 of the outer surface thereof, which extends between the second opening 52 and the minor unbonded area 68, which is not bonded with the first face 48 of the second elastic patch 46. Once the valve assembly is assembled together, it may be joined with the implant shell by vulcanization, adhesives, or glue.

Figure 6B:
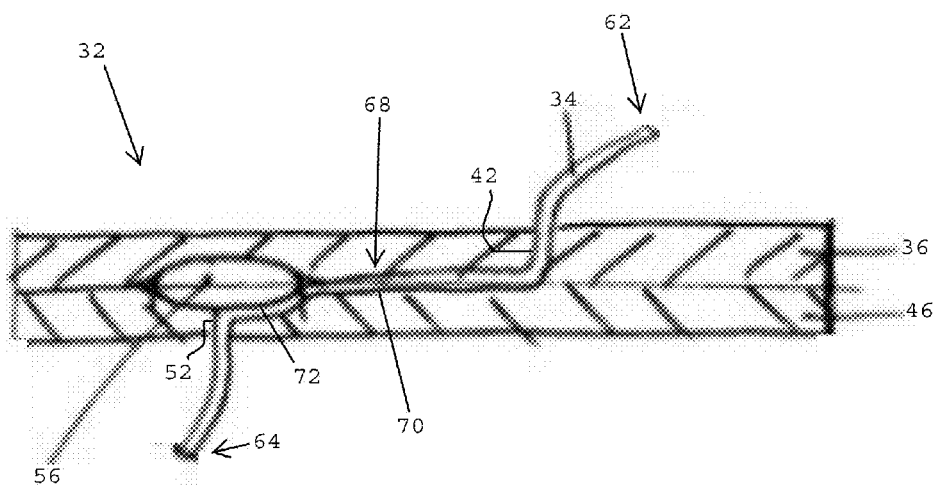
FIG. 6B shows the valve assembly of FIG. 6A with the filling tube of FIG. 5 extending through the valve assembly, in accordance with one embodiment of the present invention.

Referring to FIG. 6B, in one embodiment, the elongated filling tube 34 is placed onto a stump prick tool (not shown) and the second end 64 of the elongated filing tube 34 is advanced through the first opening 42 of the first elastic patch 36, through the elongated channel 70 of the minor unbonded area 68, around the unbonded first section 72 of the outer surface of the plug 56 and through the second opening 52 of the second elastic patch 46. In one embodiment, the valve assembly 32 is opened when the elongated filling tube 34 is passed through the valve assembly and closed when the elongated filling tube 32 is removed from the valve assembly.

Figure 7A:
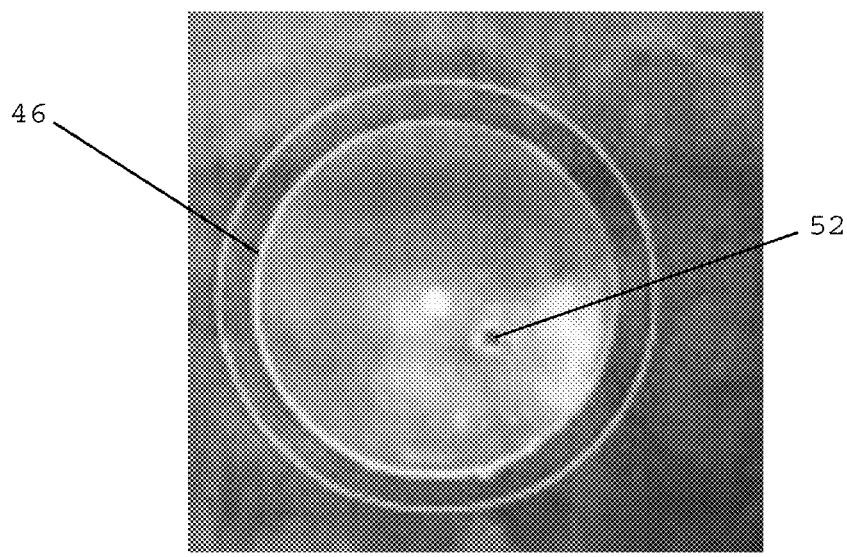
FIGS. 7A-7M show a method of making a valve assembly for an expandable implant device, in accordance with one embodiment of the present invention.

FIGS. 7A-7M show a method of making a valve assembly, in accordance with one embodiment of the present invention. Referring to FIG. 7A, in one embodiment, a second elastic patch 46 made of silicone is placed atop a surface. The second elastic patch 46 has a second opening 52 extending therethrough that is offset from a center of the second elastic patch 46.

Figure 7B:
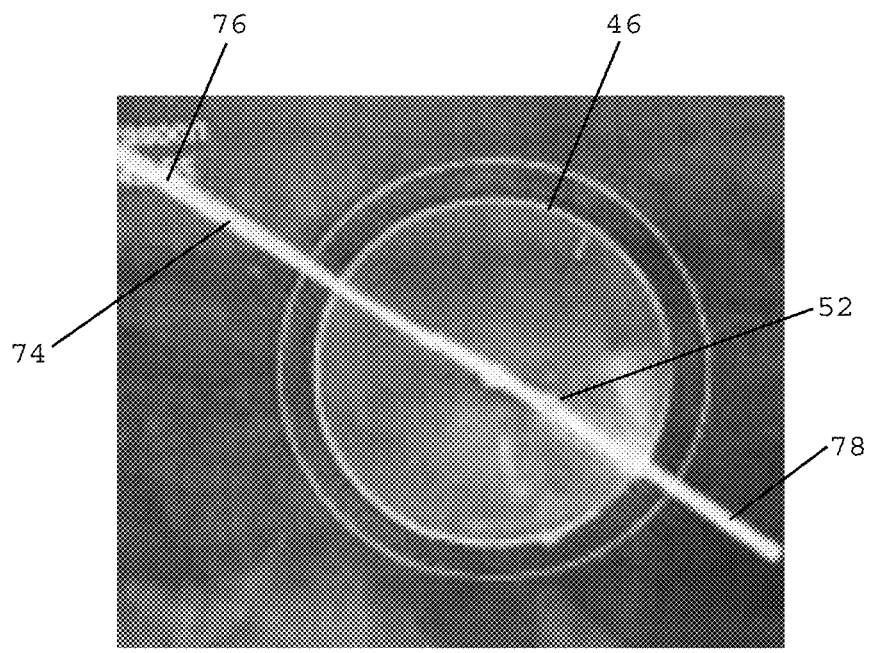

Referring to FIG. 7B, a polymer or non-stick strip 74 is passed through the second opening 52 so that a first section 76 of the strip 74 lies above the second elastic patch 46 and a second section 78 lies below the second elastic patch 46.

Figure 7C:
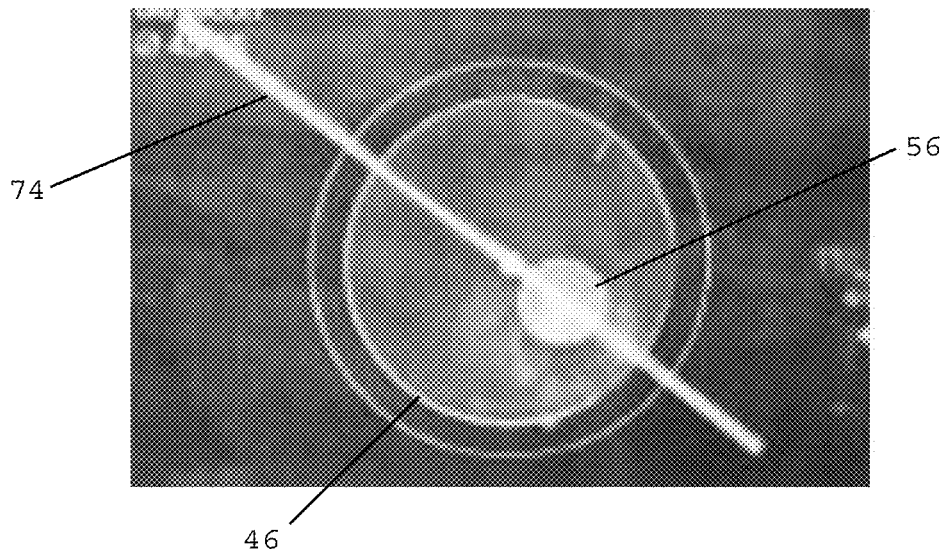
Figure 7D:
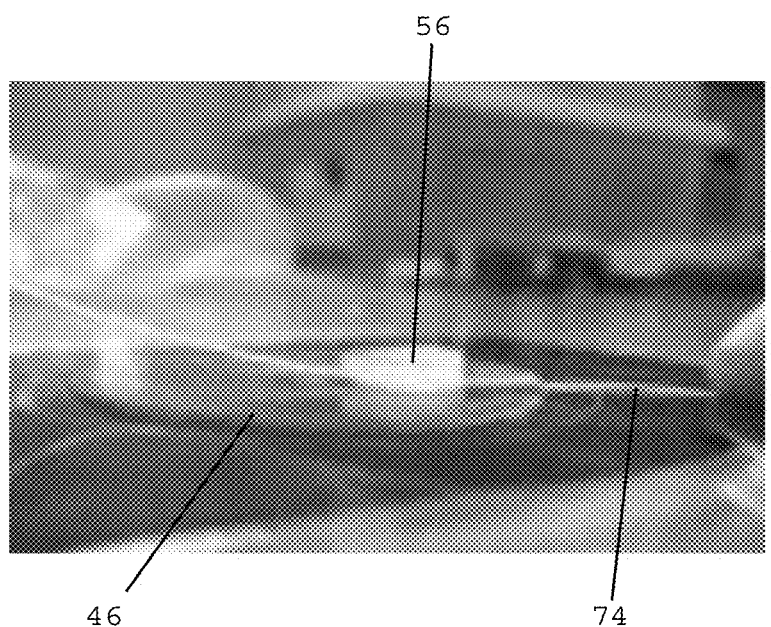

Referring to FIGS. 7C and 7D, a plug 56 that is thicker and less elastic than the second elastic patch 46 is placed atop the second elastic patch 46. The plug 56 is aligned with the second opening 52 (FIG. 7A) extending through the second elastic patch 46 and sits atop a portion of the strip 74 passing through the second opening 52.

Figure 7E:
Figure 7F:
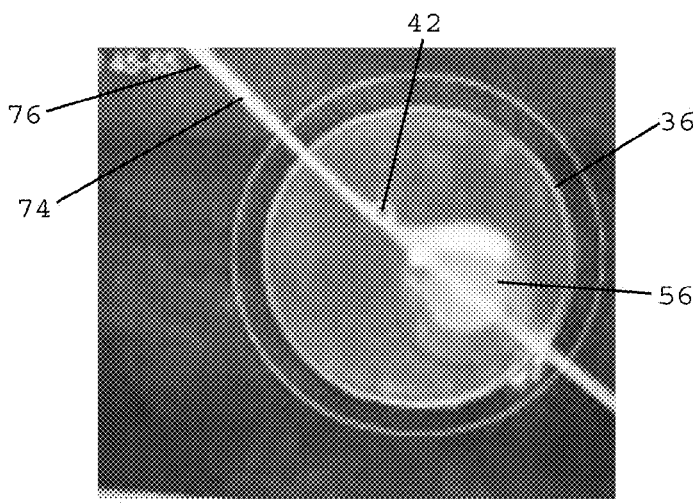
Figure 7G:
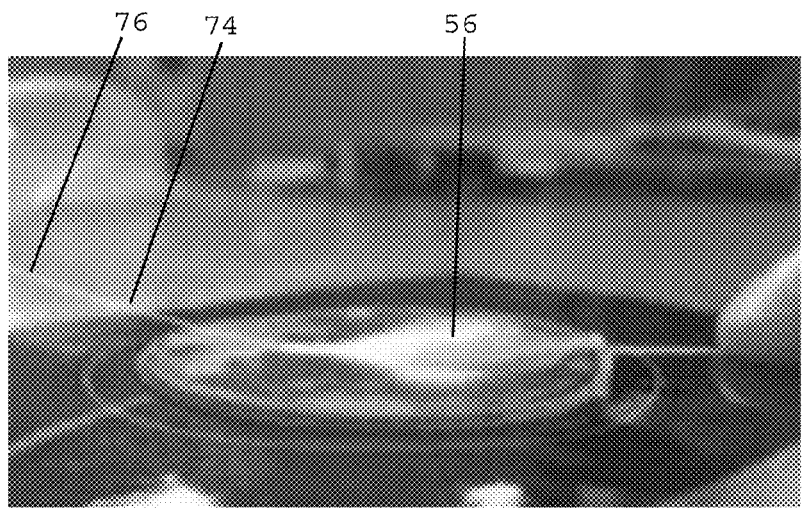

Referring to FIGS. 7E-7G, the first elastic patch 36 with the first opening 42 (FIG. 6A) is placed over the plug 56 and the strip 74. The first end 76 of the strip 74 is passed through the first opening 42 of the first elastic patch 36. Major areas of the opposing faces of the first and second elastic patches are bonded together, such as by being vulcanized together.

Figure 7H:
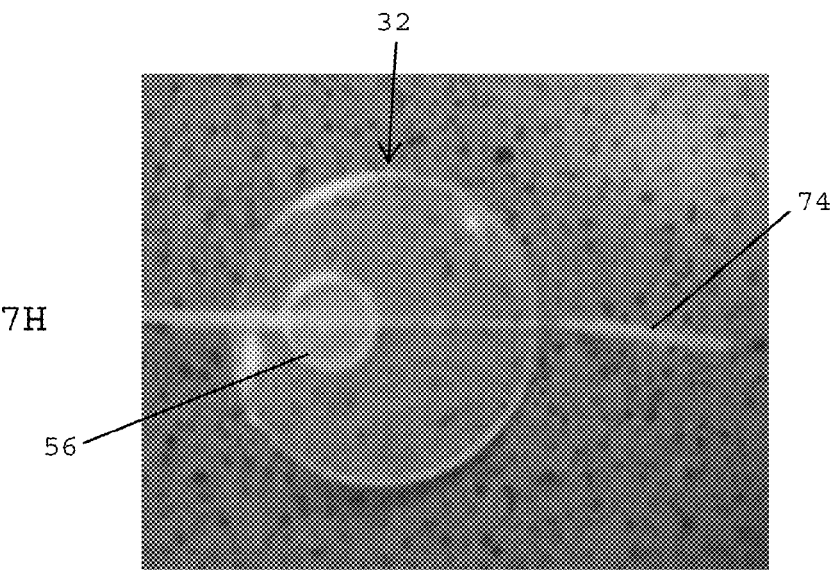
Figure 7I:
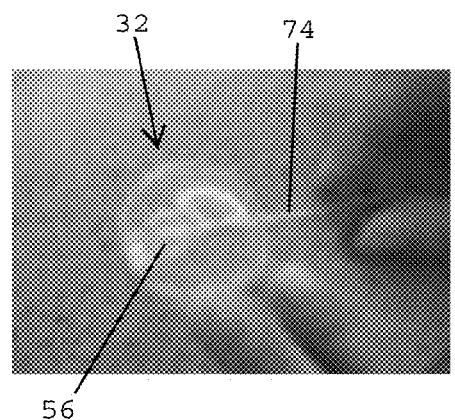
Figure 7J:
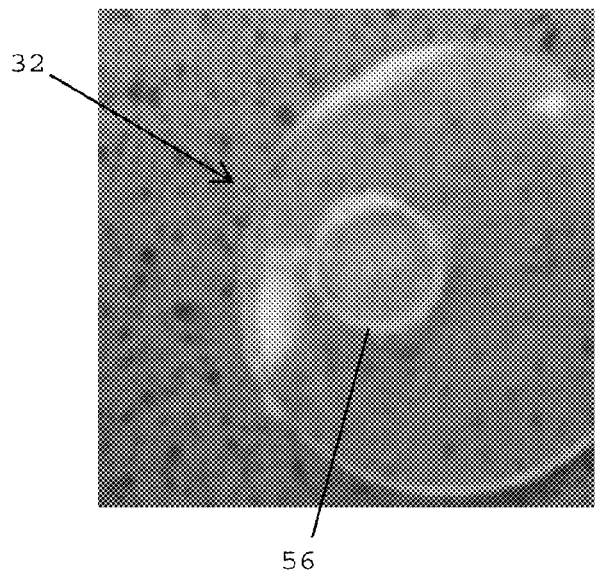

Referring to FIGS. 7H-7J, the strip 74 is removed from the valve assembly 32 leaving an elongated channel, located in the minor unbonded area 68 (FIG. 6A-1), that remains open. The elongated channel extends from the first opening of the first elastic patch, through the elongated channel between the opposing faces of the first and second elastic patches, around the unbonded first section 72 (FIG. 6B) of the plug 56, and though the second opening 52 in the second elastic patch 46.

Figure 7K:
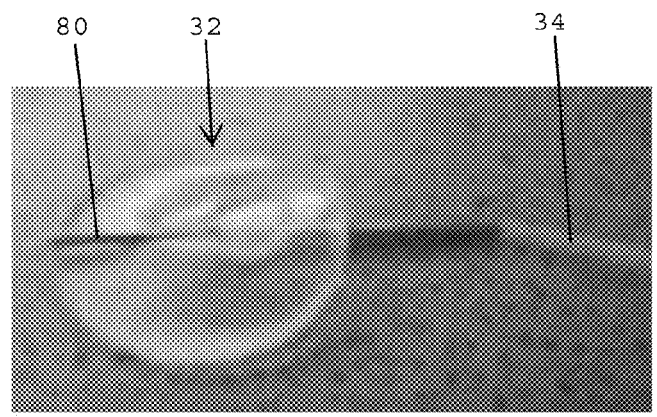
Figure 7L:
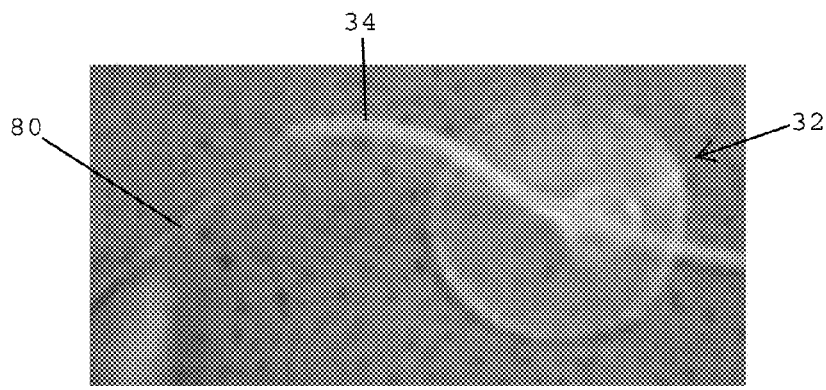

Referring to FIGS. 7K and 7L, the elongated filling tube 34 is placed on a stump prick tool 80 for inserting the elongated filling tube 34 through the elongated channel extending through the valve assembly 32.

Figure 7M:
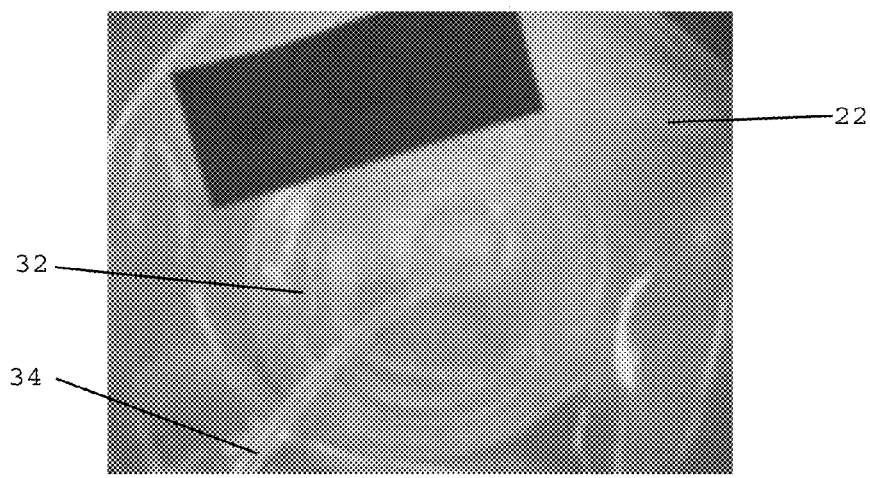

Referring to FIG. 7M, in one embodiment, the assembled valve assembly 32, with the elongated filling tube 34 passing therethrough, is secured over an opening in an implant shell 22 using an un-vulcanized silicone ring followed by a vulcanization process.

Figure 8A:
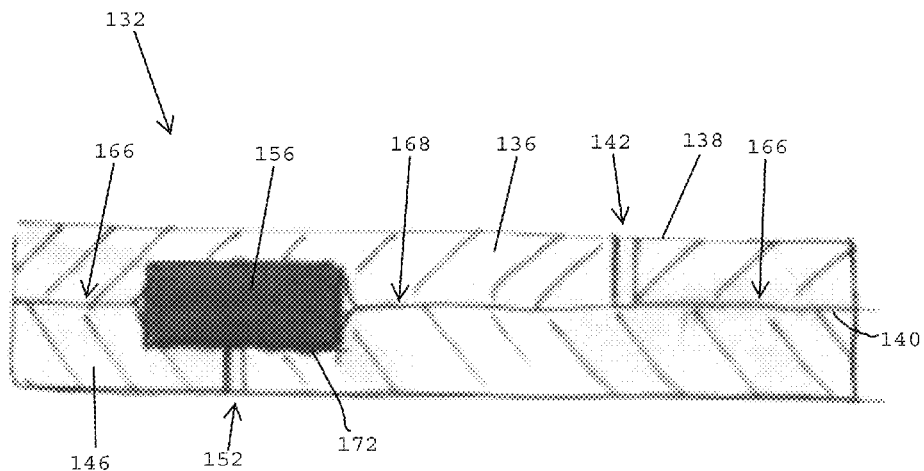
FIG. 8A shows a valve assembly for an implant, in accordance with another embodiment of the present invention.

Referring to FIG. 8A, in one embodiment, a valve assembly 132 preferably includes a plug 156, such as a circular or square disk, positioned between a first elastic patch 136 and a second elastic patch 146. The first elastic patch 136 includes a first opening 142 extending from a first surface 138 to a second surface 140. The valve assembly 132 includes a second opening 152 extending from a first surface 148 to a second surface 150. The valve assembly 132 includes a major bonded area 166 whereby the opposing face 140, 148 of the respective first and second elastic patches 136, 146 are bonded together so they are not free to move away from one another under stress forces. The valve assembly 132 includes a minor unbonded area 168 that includes an elongated channel extending between the first opening 142 in the first elastic patch 136 and the second opening 152 in the second elastic patch 146. The minor unbonded area 168 extends over at least a first section 172 of the outer surface of the plug 156 so that the opposing surface of the second elastic patch 146 may move away from the first section 172 of the plug 156.

Figure 8B:
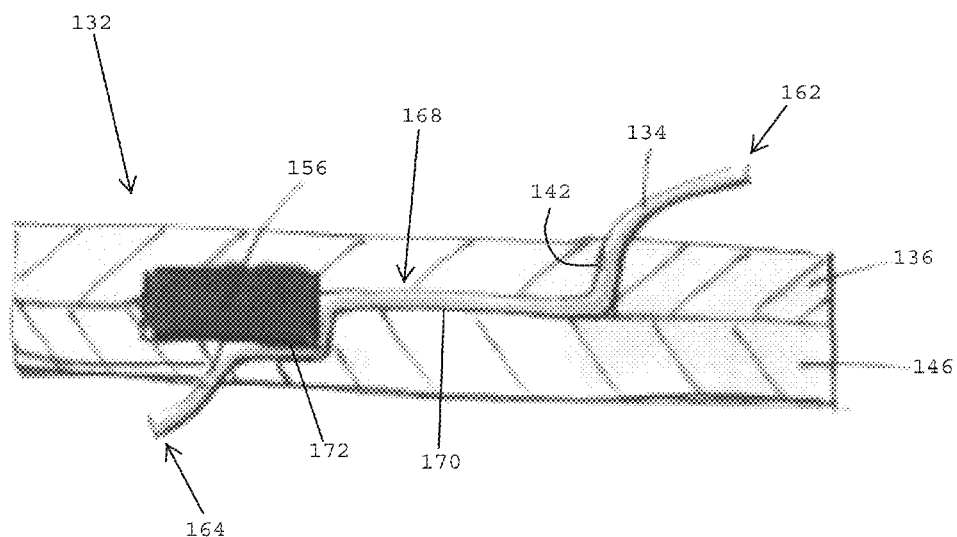
FIG. 8B shows the valve assembly of FIG. 8A and a filling tube passing therethrough, in accordance with one embodiment of the present invention.

Referring to FIG. 8B, in one embodiment, an elongated filling tube 134 may be passed through the minor unbonded area 168 of the valve assembly that extends between the first elastic patch 136 and the second elastic patch 146. In one embodiment, a stump prick tool is passed through the elongated filling tube 134 so that the second end 164 of the elongated filling tube 134 may be advanced through the first opening 142 of the first elastic patch 168, the elongated channel 170 of the minor unbonded area 168 extending between the opposing faces of the first and second elastic patches, around the unbonded first surface 172 of the plug 156, and through the second opening 152 of the second elastic patch 146. After the elongated filling tube 134 has been passed through the valve assembly 132, the second end 164 of the elongated filling tube 134 is located inside the implant shell and the first end 162 of the elongated filling tube is located outside the implant shell.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. An expandable implant comprising:
   an implant shell having an outer surface, an inner surface, and an opening extending from the outer surface to the inner surface;
   a valve assembly closing said opening in said implant shell, said valve assembly comprising
   a first elastic patch,
   a second elastic patch juxtaposed with said first elastic patch, wherein a major face of said first elastic patch opposes a major face of said second elastic patch, and wherein the opposing major faces have a bonded area in which the opposing major faces are joined together and an unbonded area in which the opposing major faces are free to move away from one another,
   a plug disposed between the opposing major faces of said first and second elastic patches,
   a first opening extending through said first elastic patch and being in communication with said unbonded area,
   a second opening extending through said second elastic patch and being in communication with said unbonded area, wherein said second opening is offset from said first opening, said unbonded area defining an elongated channel extending between said first and second openings of said first and second elastic patches, said elongated channel having a proximal end and a distal end, wherein said plug is located between the distal end of said elongated channel and said second opening of said second elastic patch, and wherein said plug is spaced from the proximal end of said elongated channel and said first opening of said first elastic patch.

2. The implant as claimed in claim 1, wherein said plug has less elasticity than said first and second elastic patches.

3. The implant as claimed in claim 1, wherein the opposing major faces of said elastic patches are free to move away from one another within said elongated channel.

4. The implant as claimed in claim 1, further comprising a filling tube extending through said valve assembly from outside said implant shell to inside said implant shell for opening said valve assembly for inflating and deflating said implant.

5. The implant as claimed in claim 4, wherein said filling tube passes through said first opening in said first elastic patch, through said elongated channel between said first and second openings, around a first section of an outer surface of said plug, and through said second opening in said second elastic patch.

6. The implant as claimed in claim 5, wherein a first section of said outer surface of said plug is unbonded to said second elastic patch, a second section of said outer surface of said plug is bonded to said second elastic patch, and a third section of said outer surface of said plug is bonded to said first elastic patch.

7. The implant as claimed in claim 5, wherein said plug is disposed between the opposing major faces of said first and second elastic patches and aligned with said second opening in said second elastic patch.

8. The implant as claimed in claim 1, wherein said first and second elastic patches are substantially planar, and said plug has a shape selected from the group consisting of circular, ellipsoid, oblate spheroid, square and rectangular.

9. The implant as claimed in claim 1, wherein said plug has a thickness that is greater than the thickness of each of said first and second elastic patches.

10. The implant as claimed in claim 9, wherein said plug has a thickness of about 2-5 mm, each said elastic patch has a thickness of about 0.25-1.0 mm.

11. A valve assembly for an expandable implant comprising:
a first elastic patch;
a second elastic patch juxtaposed with said first elastic patch, wherein a major face of said first elastic patch opposes a major face of said second elastic patch, and wherein the opposing major faces have a bonded area in which the opposing major faces are joined together and an unbonded area in which the opposing major faces are free to move away from one another;
a plug disposed between the opposing major faces of said first and second elastic patches, wherein said plug has less elasticity than said first and second elastic patches;
a first opening extending through said first elastic patch and being in communication with said unbonded area;
a second opening extending through said second elastic patch and being in communication with said unbonded area, wherein said second opening is offset from said first opening;
said unbonded area defining an elongated channel extending between said first and second openings and the opposing major faces of said first and second elastic patches, wherein the opposing major faces along said elongated channel are free to move away from one another, and wherein said plug is located between a distal end of said elongated channel and said second opening of said second elastic patch and said plug is spaced from a proximal end of said elongated channel and said first opening of said first elastic patch.

12. The valve assembly as claimed in claim 11, further comprising a filling tube passing through the first opening, through the elongated channel, around at least a first section of said plug, and through the second opening.

13. The valve assembly as claimed in claim 11, wherein said plug has an outer surface including a first section that is in contact with and unbonded to said second elastic patch, a second section that is bonded to said second elastic patch, and a third section that is bonded with said first elastic patch.

14. The valve as claimed in claim 11, wherein said plug has a thickness that is greater than the thickness of each of said first and second elastic patches.

15. The valve as claimed in claim 14, wherein said plug has a thickness of about 2-5 mm and a diameter of about 7-12 mm.

16. The valve as claimed in claim 14, wherein each said elastic patch has a thickness of about 0.25-1.0 mm and a diameter of about 30-50 mm.

17. The valve as claimed in claim 11, wherein said plug comprises a material selected from the group consisting of silicone, vulcanized silicone, silicone gel, LSR elastomer, and high-consistency elastomer.

18. The valve as claimed in claim 11, wherein said elastic patches comprise a material selected from the group consisting of silicone, LSR elastomer, and high-consistency elastomer.

19. The valve as claimed in claim 11, wherein said plug has a shape selected from the group consisting of circular, spheroid, ellipsoid, square and rectangular.

20. A valve assembly for an expandable implant comprising:
a first elastic patch;
a second elastic patch juxtaposed with said first elastic patch, wherein opposing major faces of said elastic patches have a bonded area in which the opposing major faces are joined together and an unbonded area in which the opposing major faces are free to move away from one another;
a plug disposed between the opposing major faces of said first and second elastic patches, wherein said plug has less elasticity than said first and second elastic patches;
a first opening extending through said first elastic patch and being in communication with said unbonded area;
a second opening extending through said second elastic patch and being in communication with said unbonded area, wherein said second opening is offset from said first opening;
said unbonded area defining an elongated channel extending between said first and second openings and the opposing major faces of said first and second elastic patches; and
a flexible filling tube passing through said first opening, said elongated channel, around a section of said plug, and through said second opening for opening said valve assembly, wherein said flexible filling tube changes direction a first time between said first opening and said elongated channel, a second time between said elongated channel and said plug, and a third time between said plug and said second opening.

21. The valve assembly as claimed in claim 20, wherein said plug is located at a distal end of the elongated channel and is in alignment with the second opening of said second elastic patch and said plug is spaced away from a proximal end of the elongated channel and is spaced away from the first opening of said first elastic patch.

* * * * *